United States Patent
Godoy et al.

(10) Patent No.: US 8,393,249 B2
(45) Date of Patent: Mar. 12, 2013

(54) ELECTROMAGNETIC SUPPORT COIL AND SUBFRAME

(76) Inventors: Arthur Alexander Godoy, Surrey (CA); Stephen Andrew Godoy, Long Beach, CA (US)

( * ) Notice: Subject to any disclaimer, the term of this patent is extended or adjusted under 35 U.S.C. 154(b) by 264 days.

(21) Appl. No.: 12/972,354

(22) Filed: Dec. 17, 2010

(65) Prior Publication Data

US 2011/0152911 A1   Jun. 23, 2011

Related U.S. Application Data

(60) Provisional application No. 61/287,801, filed on Dec. 18, 2009.

(51) Int. Cl.
*B43K 5/00* (2006.01)
*B26F 1/00* (2006.01)
*A61B 17/34* (2006.01)

(52) U.S. Cl. ............................ 81/9.22; 606/186; 30/362

(58) Field of Classification Search ................. 81/9.22; 606/186; 30/362
See application file for complete search history.

(56) References Cited

U.S. PATENT DOCUMENTS

| 4,159,659 | A  | * | 7/1979 | Nightingale | 81/9.22 |
| 6,950,004 | B2 | * | 9/2005 | Godoy et al. | 336/160 |
| 7,748,294 | B2 | * | 7/2010 | Jarboe et al. | 81/9.22 |
| 2008/0200942 | A1 | * | 8/2008 | Beyer | 606/186 |
| 2008/0300615 | A1 | * | 12/2008 | Colton et al. | 606/186 |
| 2009/0090218 | A1 | * | 4/2009 | Jarboe et al. | 81/9.22 |
| 2009/0183602 | A1 | * | 7/2009 | Crockett | 81/9.22 |
| 2010/0241151 | A1 | * | 9/2010 | Rickard | 606/186 |
| 2011/0125179 | A1 | * | 5/2011 | Dell'Aquila et al. | 606/186 |
| 2011/0146453 | A1 | * | 6/2011 | Forth | 81/9.22 |

* cited by examiner

*Primary Examiner* — David B Thomas
(74) *Attorney, Agent, or Firm* — Laurence C. Bonar (57) ABSTRACT

An improved electromagnetic coil tattoo machine offers the operator the opportunity to customize the machine's structural and operating properties. An embodiment of the invention provides a tattoo machine having at least one electromagnetic support coil which may include a coil core which has threaded holes which accommodate fasteners used to structurally secure and support 2 or 3 piece sub-frame members which house the secondary components that a conventional one-piece frame would house—such as the spring/armature bar, the binding posts and the preferred tube vice system. Accordingly in one embodiment, the support coil assemblies themselves act as a primary structural frame member. In a further embodiment, the electromagnetic support coil assembly may also use removable instead of non-removable retaining washers and O-rings to retain magnetic wire windings such as to allow the operator to customize and repair the magnetic wire.

20 Claims, 5 Drawing Sheets

ELECTROMAGNETIC SUPPORT COIL AND SUBFRAME

RELATED APPLICATION

The present application claims priority to the following previously filed patent application: U.S. Provisional Patent Application No. 61/278,801, filed Dec. 18, 2010 and entitled "Electromagnetic Support Coil and Subframe", the contents of which are herein incorporated by reference in their entirety.

FIELD OF THE INVENTION

The present invention relates generally to the field of tattooing and tattoo machines, and more particularly to electromagnetic tattoo machines having improved electromagnetic support coil assemblies which provide structural support for other tattoo machine components.

BACKGROUND TO THE INVENTION

The electromagnetic coil assembly is one of the most important components of any tattoo machine that uses electromagnetism to operate. The electromagnetic coil assembly provides a reciprocating or oscillating motion to a spring mounted magnetic armature bar which in turn drives the reciprocating motion of the tattoo needle for transferring tattoo ink to the subject's skin. In common existing electromagnetic tattoo machine coil and tattoo machine frame technology a solid "one piece" structural frame component is used to support and house the electromagnetic coil assembly and other tattoo machine components. The single solid structural frame component commonly used in such existing tattoo machines may typically limit the range of adjustment of the moving parts of the machine, such as the armature bar and needle bar, and the non-moving parts such as the needle tube. Such single solid structural frame designs may also typically use fixed retaining washers to attach the electromagnetic coil assemblies to the frame, which may limit the adjustability or accessibility of the magnetic wire windings of the coils, such as for custom adjustment or repair, for example.

BRIEF SUMMARY OF THE INVENTION

According to an embodiment of the present invention, an object of the V3 Electromagnetic Support Coil Bobbin Assembly (such as shown in more detail in FIG. 4) is to provide an improved electromagnetic tattoo machine with improved performance such as providing for facilitated removal and replacement of retaining washers and O-rings such as between electromagnetic coils and frame members, and to enable a machine operator to further customize, not only the electromagnetic coil's wire windings, but the configuration of the machine as a whole, which may not be possible with traditional "one piece frame" tattoo machines.

According to another embodiment of the present invention, a tattoo machine having one or more electromagnetic support coil assemblies is provided to improve, increase and focus the electromagnetism that is generated by the coil. The one or more electromagnetic support coil assemblies may have one or more threaded holes which accommodate screws or other fasteners used to structurally secure and support sub-frame members which may house the secondary supporting components of the tattoo machine that a standard traditional "one piece" frame would conventionally house. In one embodiment, the shape of the electromagnetic support coil may vary, such as a conventional round coil core and winding, or a rectangular core and winding, and/or a substantially square electromagnetic coil core or bobbin, for example, as is shown in the exemplary embodiment of FIG. 4.

In another embodiment of the present invention, a tattoo machine is provided, comprising:

at least one electromagnetic support coil assembly comprising a coil core having an upper end and a lower end, and at least one wire winding around said coil core, wherein said upper end of said coil core comprises a mounting flange;

at least one upper sub-frame member structurally attached to and supported by said mounting flange of said coil core upper end;

an armature bar attached to said at least one upper sub-frame member and adapted to move in a reciprocating manner towards and away from said upper end of said coil core; and a base sub-frame member structurally attached to and supported by said lower end of said coil core, wherein said base sub-frame member is adapted to support a needle tube.

In yet a further embodiment of the present invention, an electromagnetic support assembly for a tattoo machine is provided, comprising:

a coil core having an upper end and a lower end;

at least one wire winding around said coil core;

wherein said upper end of said coil core comprises a mounting flange having at least one threaded hole extending into a side surface of said mounting flange adapted for supportive structural attachment to at least one tattoo machine upper sub-frame member using one or more threaded fasteners; and wherein said lower end of said coil core comprises at least one threaded hole extending into said lower end of said coil core and is adapted for supportive structural attachment to a tattoo machine base sub-frame member using one or more threaded fasteners.

Further embodiments of the present invention are detailed below.

BRIEF DESCRIPTION OF THE SEVERAL VIEWS OF THE DRAWINGS

The apparatus and method of the present invention will now be described with reference to the accompanying drawing figures, in which.

DETAILED DESCRIPTION OF SEVERAL EMBODIMENTS

Figure 1:
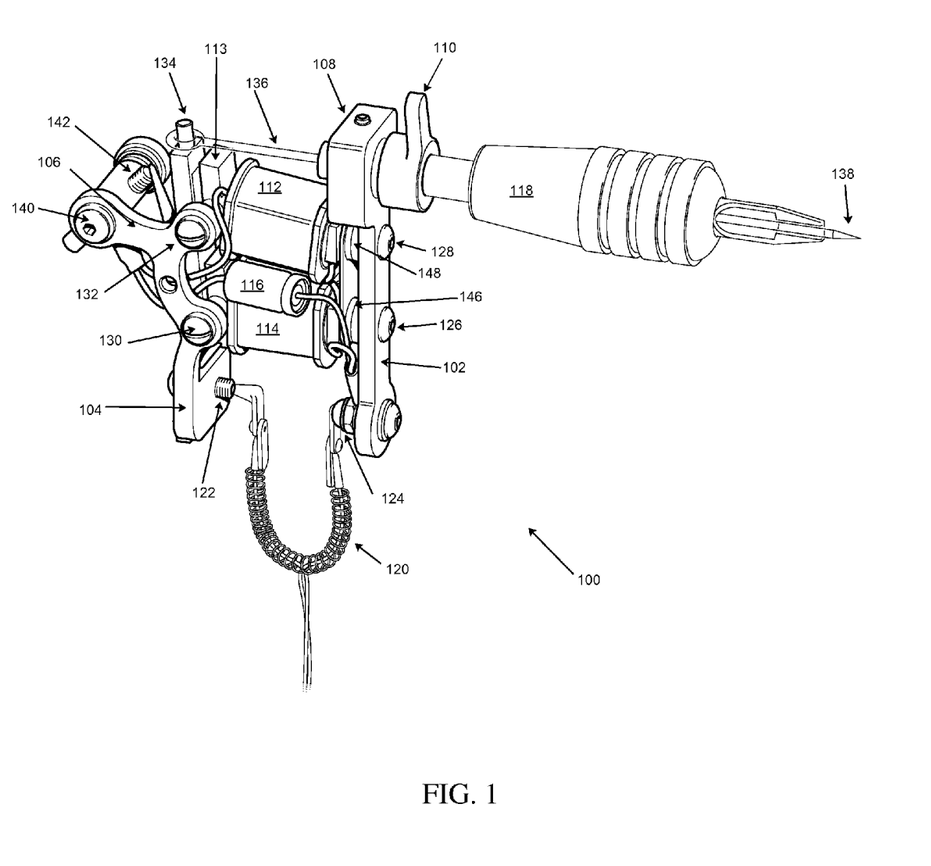
FIG. 1 illustrates a perspective view of a tattoo machine according to an embodiment of the invention having an electromagnetic support coil assembly and assembled in an exemplary right handed configuration with a two piece support sub-frame.

FIG. 1 illustrates a perspective view of an electromagnetic tattoo machine 100 according to an embodiment of the invention having an electromagnetic support coil assembly 112, 114, and assembled in an exemplary right handed configuration with a two piece support sub-frame comprising a base sub-frame 102 and an upper binding post/saddle sub-frame 104. The base sub-frame 102 may comprise coil mounting spacers 146, 148 adapted for mounting electromagnetic coil assemblies 114 and 112, respectively, such as by means of lower coil mounting screws 126 and 128, for example. The upper binding post/saddle sub-frame 104 may comprise an upper binding post 142 held by an upper binding post bolt 140, and extending from a saddle 106 of the upper binding post/saddle sub-frame 104. The upper binding post/saddle sub-frame 104 may be mounted to the side of an upper mounting flange 113 of the electromagnetic coil assemblies 112 and 114 such as by upper coil mounting screws 132 and 130, respectively, for example. In the embodiment illustrated in FIG. 1, electromagnetic coil assemblies 112 and 114 are also connected to a capacitor, such as exemplary axial electrolytic capacitor 116, which may be connected in parallel with coil assemblies 112, 114, for example.

An armature bar 134 comprised of a ferrous or other magnetically attracted material is attached to the saddle sub-frame 104 and extends along the top sides of electromagnetic coil assemblies 112, 114. The armature bar 134 is spring biased towards the upper binding post 142 and is thereby adapted to reciprocate AC power is applied to the coil assemblies 112, 114, such that the armature bar 134 is alternately magnetically attracted to the coil assemblies 112, 114, and then retracted by a spring biasing force towards the upper binding post 142, for example. A power cord 120 connects AC power to the electromagnetic coil assemblies 112, 114 by means of upper binding post connector 112 and lower binding post connector 124, for example.

In one embodiment, a needle bar 136 may typically be attached to the armature bar 134 to transmit the reciprocating motion of the armature bar to a needle or needle grouping 138 at the tip of the needle bar 136, which may be used to inject ink into the skin of a human or animal subject when the tattoo machine 100 is in use. A hollow housing or tube grip 118 is placed over the needle bar 136 to guide the reciprocating motion of the needle bar 136. In one embodiment, a tube grip vise such as an exemplary screw-tight tube vise 110 (such as is disclosed in U.S. Pat. No. 6,772,656, the contents of which are herein incorporated by reference in their entirety) may be used to retain the tube grip 118 in the upper end 108 of the base sub-frame 102, while allowing the reciprocating needle bar 136 to pass through the base sub-frame 102.

In the present embodiment, one or more of electromagnetic coil assemblies 112, 114 of tattoo machine 100 preferably comprise electromagnetic support coils or support coil assemblies 112, 114, which desirably function as a structural support for attachment of one or more upper and lower support sub-frame components, in addition to their function as an electromagnetic coil. In particular, such support coil assemblies 112, 114 function to provide a structural support and connection between a lower sub-frame such as base sub-frame 102, and at least one upper sub-frame, such as upper binding post/saddle sub-frame 104. In the present embodiment illustrated in FIG. 1, support coil assemblies 112 and 114 provide structural support and connection between upper sub-frame 104 and lower base sub-frame 102 by means of structural connection with upper coil mounting screws 132, 130 to at least one threaded (such as by drilling and tapping) hole in the upper side of mounting flange 113 of the support coil assemblies 112, 114, and structural connection with lower coil mounting screws 128, 126 to at least one threaded (such as by drilling and tapping) hole in the lower end of the support coil assemblies 112, 114. Accordingly, the support coil assemblies 112, 114, thereby form the central portion of the structure of the tattoo machine 100, and avoid the need for additional structural frame components extending between the upper and lower sides of the coil assemblies 112, 114, and may thereby desirably provide one or more of: increased simplicity, reduced weight, improved aesthetics and improved adjustability and configurability of the tattoo machine 100.

According to one embodiment of the present invention, the use of multiple piece sub-frames such as upper sub-frame 194 and base sub-frame 102 (or three piece sub-frame components in other embodiments) attached to the at least one electromagnetic support coil assemblies 112, 114, may desirably lessen the weight of a traditional one piece tattoo machine frame by eliminating the whole middle section of the conventional one piece frame which would have been used to attach and support the conventional coils. Further weight reduction may also optionally be achieved by manufacturing using lighter metals such as aluminum, titanium and even non-metal materials such as plastics, nylon, composites, poly carbonates, or even wood, to provide at least one of the sub-frame components.

In one embodiment, a tattoo machine 100 according to the invention may be customized to include either a two piece sub-frame (comprising upper sub-frame 104 and base sub-frame 102) or alternatively a three piece sub-frame. In one such embodiment, a two piece sub-frame configuration such as is illustrated in FIG. 1, the upper binding post/saddle sub-frame 104 may be fabricated out of any suitable non-metal and/or non-ferrous material, and may desirably be separated from contact with the electromagnetic support coil assemblies 112, 114 by non ferrous and/or non-metal washers or spacers such as coil mounting spacers 146, 148. The support coil assemblies 112, 114, may preferably be attached to the sub-frame components 102, 104 such as by suitable non-ferrous and/or non-metal screws in order to further magnetically separate and isolate the support coils 112, 114, from the sub-frame components 102, 104. In some embodiments, such magnetic separation may in turn improve focus of the magnetic field generated by the electromagnetic support coil assemblies 112, 114, to act on the armature bar 134, and may desirably reduce leakage and/or dissipation of the generated magnetic field such as by absorption by or action on the "non-moving" parts (i.e. parts other than armature bar 134) of the tattoo machine 100 which have no need for influence by the generated magnetic field for them to function during operation of the tattoo machine 100.

In another embodiment, the base sub-frame 102 may be controllably further physically and/or magnetically separated from the one or more support coil assemblies 112, 114 and in particular the mounting flanges 113 of the core elements of the support coil assemblies 112, 114, with one or more spacing washers, such as exemplary non-ferrous and/or non-metal washers, to focus the support coil-generated magnetic field on the armature bar 134. Such additional separation may also desirably further separate and magnetically isolate the support coil assemblies 112, 114 to desirably reduce leakage and/or dissipation of the generated magnetic field on "non-moving" parts (i.e. parts other than the armature bar 134) which have no need for a magnetic field for them to function (such as the common steel securing screws, metal base, frame and bracket components made of iron, steel, aluminum, etc. as may commonly be used in a conventional tattoo machine with a one piece frame design and no structural supporting function of the coil assemblies). Accordingly, in some embodiments, the support coil assemblies 112, 114, may desirably be attached to the base sub-frame 102 and/or the upper binding post and/or saddle sub-frame 104 with any suitable non-ferrous fasteners such as exemplary non-ferrous screws 126, 128, 130 and 132, and may also include one or more spacing washers, where said fasteners and spacing washers may desirably be made of plastic, brass, nylon, or other suitable non-ferrous and optionally also non-metal materials, for example. Any of the 2 or 3 piece support sub-frame components such as base sub-frame 102 and upper binding post/saddle sub-frame 104, may also preferably be fabricated out of any suitable non-ferrous material such as aluminum, plastics, composites, glass, or wood, for example.

Figure 2:
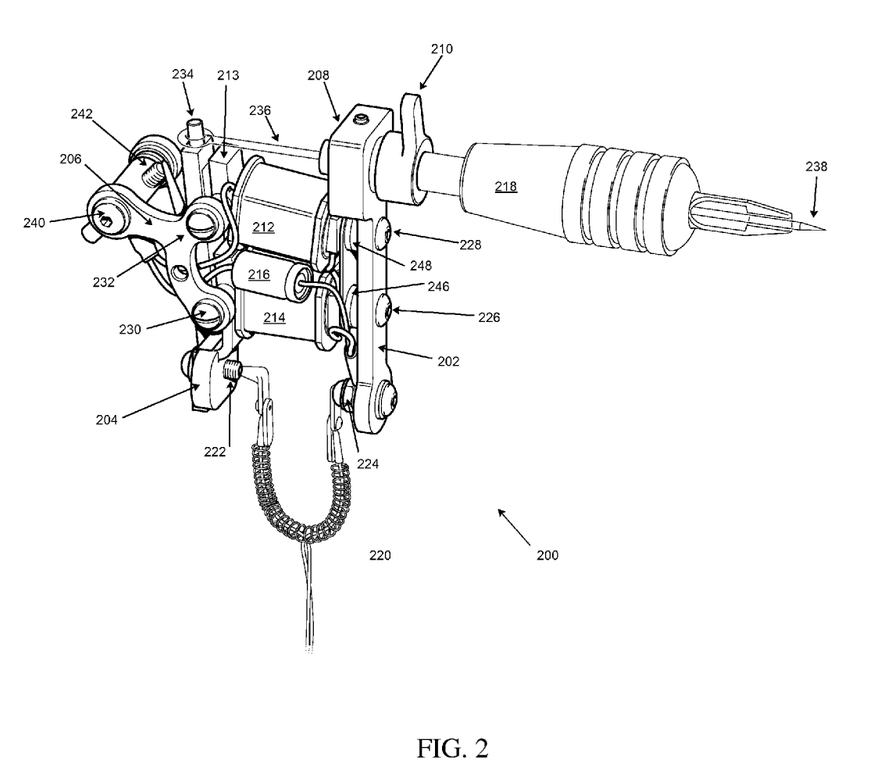
FIG. 2 illustrates a perspective view of a tattoo machine according to another embodiment of the invention having an electromagnetic support coil assembly and assembled in an exemplary left handed configuration with an exemplary three piece support sub-frame.

FIG. 2 illustrates a perspective view of an electromagnetic tattoo machine 200 according to an embodiment of the invention having electromagnetic support coil assemblies 212, 214, and assembled in an exemplary left-handed configuration with a three-piece support sub-frame comprising a base sub-frame 202, an upper binding post sub-frame 206, and a saddle sub-frame 204, to which the armature bar 234 may be spring-mounted. Similar to the embodiment of FIG. 1 above, the base sub-frame 202 may comprise coil mounting spacers 246, 248 adapted for mounting electromagnetic coil assemblies 214 and 212, respectively, such as by means of lower coil mounting screws 226 and 228, for example. The upper binding post sub-frame 206 may comprise an upper binding post 242 held by an upper binding post bolt 240, and may be mounted to the side of an upper mounting flange 213 of the electromagnetic coil assemblies 212 and 214 such as by upper coil mounting screws 232 and 230, respectively, for example. In the embodiment illustrated in FIG. 2, electromagnetic coil assemblies 212 and 214 are also connected to a capacitor, such as exemplary axial electrolytic capacitor 216, which may be connected in parallel with coil assemblies 212, 214, for example.

An armature bar 234 comprised of a ferrous or other magnetically attracted material is attached to the saddle sub-frame 204 and extends along the top sides of electromagnetic coil assemblies 212, 214. The armature bar 234 is spring biased towards the upper binding post 242 and is thereby adapted to reciprocate AC power is applied to the coil assemblies 212, 214, such that the armature bar 234 is alternately magnetically attracted to the mounting flange 213 of the coil assemblies 212, 214, and then retracted by a spring biasing force towards the upper binding post 242, for example. A power cord 220 connects AC power to the electromagnetic coil assemblies 212, 214 by means of upper binding post connector 212 and lower binding post connector 224, for example.

Similar to as above in FIG. 1, in one embodiment, the needle bar 236 may typically be attached to the armature bar 234 to transmit the reciprocating motion of the armature bar to a needle or needle grouping 238 at the tip of the needle bar 236, which may be used to inject ink into the skin of a human or animal subject when the tattoo machine 200 is in use. A hollow housing or tube grip 218 is placed over the needle bar 236 to guide the reciprocating motion of the needle bar 236. A tube grip vise such as an exemplary screw-tight tube vise 210 (such as is disclosed in U.S. Pat. No. 6,772,656) may be used to retain the tube grip 218 in the upper end 208 of the base sub-frame 202, while allowing the reciprocating needle bar 236 to pass through the base sub-frame 202.

Similar to as in FIG. 1, in one embodiment the one or more electromagnetic coil assemblies 212, 214 of tattoo machine 200 preferably comprise electromagnetic support coils or support coil assemblies 212, 214, which desirably function as a structural support for attachment of one or more upper and lower support sub-frame components, in addition to their function as an electromagnetic coil. In particular, such support coil assemblies 212, 214 function to provide a structural support and connection between a lower sub-frame such as base sub-frame 202, and the upper sub-frames, such as upper binding post sub-frame 206, and saddle sub-frame 204. In the present embodiment illustrated in FIG. 2, support coil assemblies 212 and 214 provide structural support and connection between upper sub-frames 206, and 204 and lower base sub-frame 202 by means of structural connection with upper coil mounting screws 232, 230 to at least one threaded (such as by drilling and tapping) hole in the upper side of mounting flange 213 of the support coil assemblies 212, 214, and structural connection with lower coil mounting screws 228, 226 to at least one threaded (such as by drilling and tapping) hole in the lower end of the support coil assemblies 212, 214. Accordingly, the support coil assemblies 212, 214, thereby form the central portion of the structure of the tattoo machine 200, and avoid the need for additional structural frame components extending between the upper and lower sides of the coil assemblies 212, 214, and may thereby desirably provide one or more of: increased simplicity, reduced weight, improved aesthetics and improved adjustability and configurability of the tattoo machine 200.

In one embodiment, the one or more support coil assemblies 212, 214, may be used to support the three piece sub-frame comprising the base sub-frame 202, upper binding post sub-frame 206, and saddle sub-frame 204. The sub-frames and associated components (such as upper binding post sub-frame 206, saddle sub-frame 204 and base sub-frame 202) may be fabricated out of any suitable non-ferrous and optionally also non-metal material such as those described above in reference to the embodiments of FIG. 1. The sub-frames 202, 204, 206, may also optionally be separated from the support coil assemblies 212, 214, such as by any suitable non-ferrous and/or non-metal washers or spacers, and may preferably be attached to the support coil assemblies 212, 214 by any suitable attachment, such as non-ferrous and/or non-metal screws, in order to further separate and isolate the magnetic field generated by the support coil assemblies 212, 214, which may in turn desirably help to focus the magnetic field on the armature bar 234 rather than any "non-moving" parts which have no need for a magnetic field for them to function, similar to as described above in connection with the embodiments of FIG. 1.

In another embodiment, upper binding post sub-frame 206 and its associated attached components such as binding post 242 and bolt/screw 240, may optionally be operable to allow disassembly for moving the upper binding post sub-frame 206 to attach to the opposite side of the one or more support coil assemblies 212, 214, such as to satisfy right or left handed operators. Such reversibility of the upper binding post sub-frame 206 may be further seen in comparison of the embodiments of FIG. 2 and FIG. 3 in which the upper binding post sub-frame 206 is reversed between left-handed and right-handed configurations, respectively.

In another embodiment, the spring saddle sub-frame 204, and its attached components, may optionally be removed from the tattoo machine 200 without affecting the binding posts, such as the upper binding post 242, and without changing the tension (the bend), or tuning of the rear spring component which is used to spring-mount the armature bar 234. Tuning a tattoo machine is the act of regulating the amount of bend/tension in the rear spring in conjunction with the placement of the spring on the saddle sub-frame, and tuning may typically be an exacting trial and error process, and therefore the ability to remove the spring saddle sub-frame 204 without changing the tension and/or tuning of the rear spring mechanism may be desirable to avoid the need for repetitive re-tuning of the tattoo machine 200.

Figure 3:
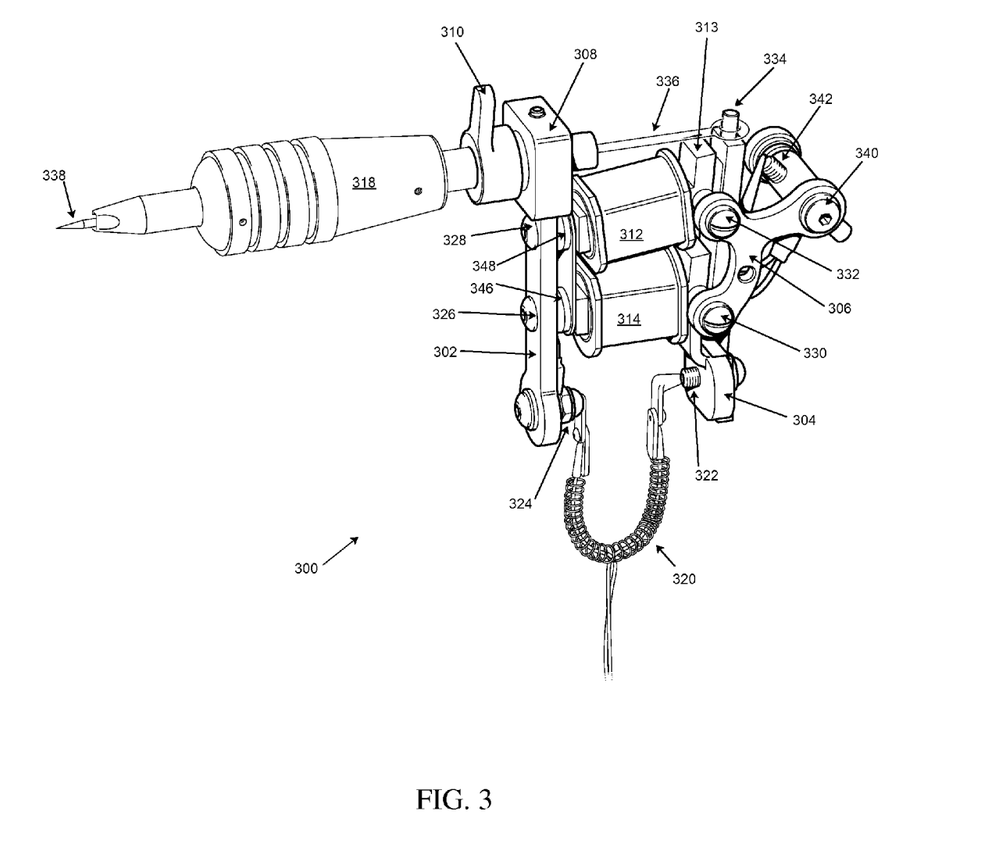
FIG. 3 illustrates a perspective view of a tattoo machine according to a further embodiment of the invention having an electromagnetic support coil assembly and assembled in an exemplary right handed configuration with an exemplary three piece support sub-frame.

FIG. 3 illustrates a perspective view of an electromagnetic tattoo machine 300 according to another embodiment of the invention having electromagnetic support coil assemblies 312, 314, and assembled in an exemplary right-handed configuration with a three-piece support sub-frame comprising a base sub-frame 302, an upper binding post sub-frame 306, and a saddle sub-frame 304, to which the armature bar 334 may be spring-mounted. Similar to the embodiment of FIG. 2 above, the base sub-frame 302 may comprise coil mounting spacers 346, 348 adapted for mounting electromagnetic coil assemblies 314 and 312, respectively, such as by means of lower coil mounting screws 326 and 328, for example. The upper binding post sub-frame 306 may comprise an upper binding post 342 held by an upper binding post bolt 340, and may be mounted to the side of an upper mounting flange 313 of the electromagnetic coil assemblies 312 and 314 such as by upper coil mounting screws 332 and 330, respectively, for example. Electromagnetic coil assemblies 312 and 314 may also be connected to a capacitor (not shown), such by connection in parallel with coil assemblies 312, 314, for example.

An armature bar 334 comprised of a ferrous or other magnetically attracted material is attached to the saddle sub-frame 304 and extends along the top sides of electromagnetic coil assemblies 312, 314. The armature bar 334 is spring biased towards the upper binding post 342 and is thereby adapted to reciprocate AC power is applied to the coil assemblies 312, 314, such that the armature bar 334 is alternately magnetically attracted to the coil assemblies 312, 314, and then retracted by a spring biasing force towards the upper binding post 342, for example. A power cord 320 connects AC power to the electromagnetic coil assemblies 312, 314 by means of upper binding post connector 312 and lower binding post connector 324, for example.

Similar to as above in FIGS. 1 and 2, in one embodiment, the needle bar 336 may typically be attached to the armature bar 334 to transmit the reciprocating motion of the armature bar to a needle or needle grouping 338 at the tip of the needle bar 336, which may be used to inject ink into the skin of a human or animal subject when the tattoo machine 300 is in use. A hollow housing or tube grip 318 is placed over the needle bar 336 to guide the reciprocating motion of the needle bar 336. A tube grip vise such as an exemplary screw-tight tube vise 310 (such as is disclosed in U.S. Pat. No. 6,772,656) may be used to retain the tube grip 318 in the upper end 308 of the base sub-frame 302, while allowing the reciprocating needle bar 336 to pass through the base sub-frame 302.

Similar to as in FIGS. 1 and 2 above, in one embodiment the one or more electromagnetic coil assemblies 312, 314 of tattoo machine 300 preferably comprise electromagnetic support coils or support coil assemblies 312, 314, which desirably function as a structural support for attachment of one or more upper and lower support sub-frame components, in addition to their function as an electromagnetic coil. In particular, such support coil assemblies 312, 314 function to provide a structural support and connection between a lower sub-frame such as base sub-frame 302, and the upper sub-frames, such as upper binding post sub-frame 306, and saddle sub-frame 304. In the present embodiment illustrated in FIG. 3, support coil assemblies 312 and 314 provide structural support and connection between upper sub-frames 306, and 304 and lower base sub-frame 302 by means of structural connection with upper coil mounting screws 332, 330 to at least one threaded (such as by drilling and tapping) hole in the upper side of the mounting flange 313 of the support coil assemblies 312, 314, and structural connection with lower coil mounting screws 328, 326 to at least one threaded (such as by drilling and tapping) hole in the lower end of the support coil assemblies 312, 314. Accordingly, the support coil assemblies 312, 314, thereby form the central portion of the structure of the tattoo machine 300, and avoid the need for additional structural frame components extending between the upper and lower sides of the coil assemblies 312, 314, and may thereby desirably provide one or more of: increased simplicity, reduced weight, improved aesthetics and improved adjustability and configurability of the tattoo machine 300.

In another embodiment, the base sub-frame 302 which typically houses the tube vice 310 and tube grip 318, may be reversible vertically to accommodate use of varying lengths of needle bars while still allowing for variable adjustment of the tube grip 318. In one such embodiment, the upper end 308 of the base sub-frame 302, may desirably be constructed with an asymmetric width or thickness relative to the lower portion of the base sub-frame 302, thereby varying the spacing of the tube vice 310 from the armature bar 334 by reversing the base sub-frame position. Such reversibility may desirably allow for use of shorter needle bars 336, such as are now standardly available paired with disposable tube grips 318 for commercial use. This reversible base sub-frame 302 allows the needle bar 336 and tube grip 318 to be moved closer to the reciprocating armature bar 334 or moved further away from the armature bar 334 if the user prefers to use shorter or longer needle bars 336 and their corresponding tube grips 318. The difference in spacing between the armature bar 334 and tube grip 318 due to the reversibility of the base sub-frame 302 may be seen by comparing the views of tattoo machine embodiments 100 or 200 shown in FIGS. 1 and 2 which show the base sub-frame in a first "forward" position, with the tattoo machine embodiment 300 shown in FIG. 3, where the base sub-frame 302 is shown in a "reversed" position where the asymmetric thickness of the upper portion 308 of base sub-frame 302 is shown extending towards the tube vice 310, rather than extending towards the armature bar as shown in the embodiments of FIGS. 1 and 2.

Similar to as described above in reference to FIG. 2, in one embodiment, the one or more support coil assemblies 312, 314, may be used to support the three piece sub-frame comprising the base sub-frame 302, upper binding post sub-frame 306, and saddle sub-frame 304. The sub-frames and associated components (such as upper binding post sub-frame 206, saddle sub-frame 204 and base sub-frame 202) may be fabricated out of any suitable non-ferrous and optionally also non-metal material such as those described above in reference to the embodiments of FIG. 1. The sub-frames 202, 204, 206, may also optionally be separated from the support coil assemblies 212, 214, such as by any suitable non-ferrous and/or non-metal washers or spacers, and may preferably be attached to the support coil assemblies 212, 214 by any suitable attachment, such as non-ferrous and/or non-metal screws, in order to further separate and isolate the magnetic field generated by the support coil assemblies 212, 214, which may in turn desirably help to focus the magnetic field on the armature bar 234 rather than any "non-moving" parts which have no need for a magnetic field for them to function, similar to as described above in connection with the embodiments of FIG. 1.

In another embodiment, similar to as described in the embodiment of FIG. 2, upper binding post sub-frame 306 and its associated attached components such as binding post 342 and bolt/screw 340, may optionally be operable to allow disassembly for moving the upper binding post sub-frame 306 to attach to the opposite side of the one or more support coil assemblies 312, 314, such as to satisfy right or left handed operators. Such reversibility of the upper binding post sub-frame 306 may be further seen in comparison of the embodiments of FIG. 2 and FIG. 3 in which the upper binding post sub-frame 306 is reversed between left-handed and right-handed configurations, respectively.

Similar to as described above in reference to FIG. 2, in another embodiment, the spring saddle sub-frame 304, and its attached components, may optionally be removed from the tattoo machine 300 without affecting the binding posts, such as the upper binding post 342, and without changing the tension (the bend), or tuning of the rear spring component which is used to spring-mount the armature bar 334. Tuning a tattoo machine is the act of regulating the amount of bend/tension in the rear spring in conjunction with the placement of the spring on the saddle sub-frame, and tuning may typically be an exacting trial and error process, and therefore the ability to remove the spring saddle sub-frame 304 without changing the tension and/or tuning of the rear spring mechanism may be desirable to avoid the need for repetitive re-tuning of the tattoo machine 300.

Figure 4:
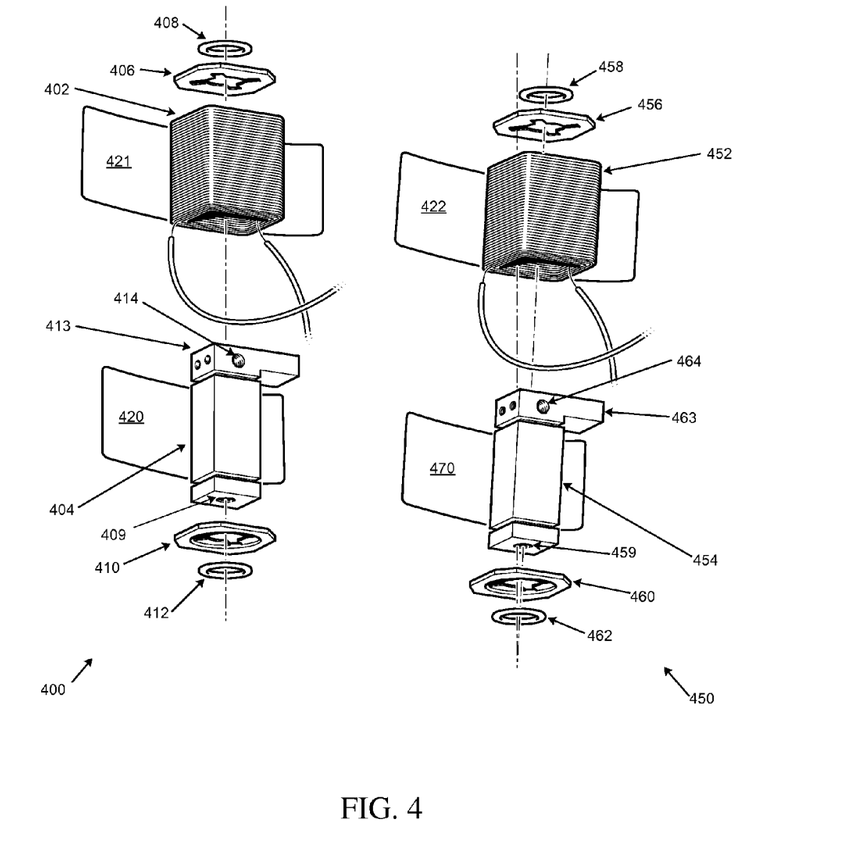
FIG. 4 illustrates an exploded perspective view of a pair of electromagnetic support coil assemblies according to a further embodiment of the invention.

FIG. 4 illustrates an exploded perspective view of a pair of electromagnetic support coil assemblies 400 and 450, according to a further embodiment of the invention. Similar to as described above, according to one embodiment of the present invention, the inventive electromagnetic support coil assemblies 400, 450, may desirably provide improvements to coil technology by changing the function of the coil post 404, 454, from not just an electromagnetic coil, but to a structurally supporting coil assembly 400, 450, functioning to accommodate one or more sub-frame support members which house secondary supporting components of a tattoo machine, such as base sub-frames 102, 202 and 302, upper binding post/saddle sub-frame 104, saddle sub-frame 204, 304, and upper binding post sub-frame 206, 306, for example. This may be accomplished by the addition of at least one attachment point, such as threaded (such as by drilling and tapping) holes 414, 464 to at least one side of the electromagnetic coil core or post members 404, 454 to allow attachment of one or more sub-frame members to establish a structural connection between the sub-frame and the support coil assembly 400, 450. For example, the threaded holes 414, 464 may formed in at least one side of the upper mounting flange 413, 463 of the coil core or post 404, 454, to allow attachment of a saddle sub-frame or combination upper binding post/saddle sub-frame component, such as by means of a core mounting screw or bolt, for example. The coil core or post 404, 454, may also preferably comprise at least one attachment point located on an end of the coil core 404, 454, such as a threaded mounting hole 409, 459 formed (such as by drilling and tapping) in an end of the coil core 404, 454, in order to provide for structural connection to another sub-frame component, such as base sub-frame 102, 202, or 302, for example.

In some embodiments, the shape of the coil core 404, 454 has been found to be important, such as the desirable use of a square core cross-section coil core 404, 454, which may desirably increase the surface area where the coil core 404, 454 contacts the typically flat armature bar component during magnetic attraction of the armature bar to the top mounting flange 413, 463 of the coil core 404, 454 during magnetization of the support coil assembly 400, 450. This is in contrast relative to the substantially smaller surface area where the top of a conventional round cross section coil core may contact the flat armature bar and may desirably result in improved magnetism, attraction of the armature bar, and general movement of the bar in a square cross section coil core 404, 454 relative to a conventional round core.

In some embodiments, the electromagnetic support coil assembly 400, 450, works in conjunction with the armature bar to power a needle bar and attached needle groupings that move in a reciprocating fashion into and out of the skin in the act of tattooing, due to the intermittent repeated electromagnetic attraction between the support coil assembly 400, 450 and armature bar when the support coil assembly 400, 450, is powered by an AC current. Increasing the amount of metal-to-metal contact between the armature bar and the upper mounting flange 413, 463 of the support coil core or post 404, 454, has been found to result in improvements in the overall functioning of the tattoo machine and the operator's ability to achieve more solid color, smoother shading, and more consistent lines, all of which depend on the rate, consistency and quality of movement of the armature bar.

In a further embodiment, the addition of one or more attachment points, such as threaded holes 414, 464 and 409, 459 to the support coil assembly 400, 450, which desirably accommodate structural attachment of the support coil assembly 400, 450 to one or more sub-frame members, thereby desirably adding to the function of the tattoo machine, as the support coil assembly 400, 450 provides the ability for the tattoo operator to further customize the structure and adjustment of the upper and lower sections of a tattoo machine as a whole, and also allows improved isolation of the main electromagnetic components which may desirably increase the effect of magnetic field, and allows focusing of the generated magnetic field on the armature bar, rather than other non-moving components of the tattoo machine.

In a particular embodiment as illustrated in FIG. 4, the electromagnetic support coil assemblies 400, 450 may comprise:

A support coil core or post 404, 454, which may comprise a cross sectional shape which may be substantially round, obround, or polygonal, and more preferably square or rectangular, and may be made of any suitable ferrous material, such as 1010- to 1025-grade steel or iron, for example. The support coil core or post 404, 454, may also comprise grooves, such as machined grooves, located substantially towards one or more of the ends of the core 404, 454, as shown in FIG. 4. In one exemplary embodiment for substantially standard size support coils, the machined grooves may measure approximately 1/16" wide by 1/16" deep, and be machined around the circumference of the core 404, 454, at substantially opposite ends of the post, starting about 1/4" in from an upper end and about 1/8" from a lower end of the coil core 404, 454. The support coil core 404, 454, may also desirably comprise at least one attachment point, such as threaded hole 414, 464, drilled through the center of the core 404, 454 from side to side, to enable structural attachment with one or more sub-frame member, such as an upper binding post sub-frame. At least one rear support coil core or post 404, 454, may have, in addition, one or more attachment points, such as threaded holes drilled from the back toward the front of the coil core 404, 454, such as to a depth about of 3/8" such as to accommodate a rear or saddle sub-frame support member to which the spring/armature bar assembly may be mounted. The coil core or post 404, 454, may optionally be coated or covered with a suitable protective and/or aesthetic material or finish, such as powder coated, painted, black zinc plated, or any other suitable finish applied to prevent oxidation while adding visual aesthetic, for example. In one embodiment, a layer of insulating tape 420, 470, such as 1 mil. polyimide insulation tape 420, 470, may optionally be placed between the coil core or post 404, 454, and magnetic wire windings;

One or more magnetic wire windings 402, 452, which may be wound on the coil core or post 404, 454, such as using AWG 22- to AWG 25-gauge magnetic copper wire for example. In one embodiment relating to a support coil for use as a front support coil at the front of a tattoo machine proximate to the needle bar, the coil core or post 404, 454, may be wound with between about 4 and 11 layers of magnetic wire. In another embodiment relating to a support coil for use as a rear support coil at the rear of a tattoo machine distal from the needle bar, the coil core or post 404, 454 may be wound with between about 4 and 10 layers of magnetic wire, and may preferably be wound with an even number of wire layers. In one preferred embodiment, the front support coil core may comprise one more layer of magnetic wire than a corresponding rear support coil;

One or more retaining washers 410, 460, located at the bottom of the windings 402, 452, and one or more retaining washers 406, 456 located at the top of the windings 402, 452, such as to secure the magnetic wire into winding layers and retain the windings 403, 452, on the support coil core or post 404, 454. In a preferred embodiment, the top 406, 456 and bottom 402, 452 retaining washers may desirably fit into and be retained by one or more grooves in the coil core or post 404, 454, such as at near the top and bottom thereof;

Optional retaining rings 412, 462 may be use at the bottom of the coil core 404, 454, and/or retaining rings 408, 458 at the top of the coil core 404, 454, such as to secure the retaining washers onto the coil core 404, 454. In one embodiment, such retaining rings may comprise O-rings made from any suitable resilient and/or elastic material, such as nitrile butadiene rubber, or "buna-n" O-rings, for example. In one embodiment of the invention, the electromagnetic support coil assembly 400, 450 may also use one or more retaining washers and/or O-rings that can be removed, allowing the operator to customize and/or repair the magnetic wire windings 402, 452 of the coil assemblies 400, 450, desirably without damaging the retaining washer and/or O-rings.

An optional insulating tape layer 421, 422 or other suitable thin and preferably durable and insulative coating material may be used to cover and protect the exterior of the magnetic wire windings 402, 452. Further, in a preferred embodiment, all visible wires may preferably be heat shrink-wrapped or otherwise insulated and protected such as from accidental contact and/or short-circuit with other objects. In another optional embodiment, a decal with a company logo or other image or graphic may also be applied to the protective tape layer 421, 422, such as for aesthetic purposes.

In a further optional embodiment, an exemplary steel or iron yoke of any suitable thickness may be used to magnetically connect the two support coil assemblies 400, 450, particularly if the bottom or base sub-frame member is made of a material which is non-ferrous. In such case, the optional iron or steel yoke may then desirably function as a magnetic bridge between a pair of support coil assemblies 400, 450. In contrast, in an embodiment where a ferro-magnetic base sub-frame support member is used, a magnetic yoke or bridge may not be needed or desired as the base sub-frame member may already function as a magnetic bridge between the attached pair of support coil assemblies 400, 450.

Figure 5A:
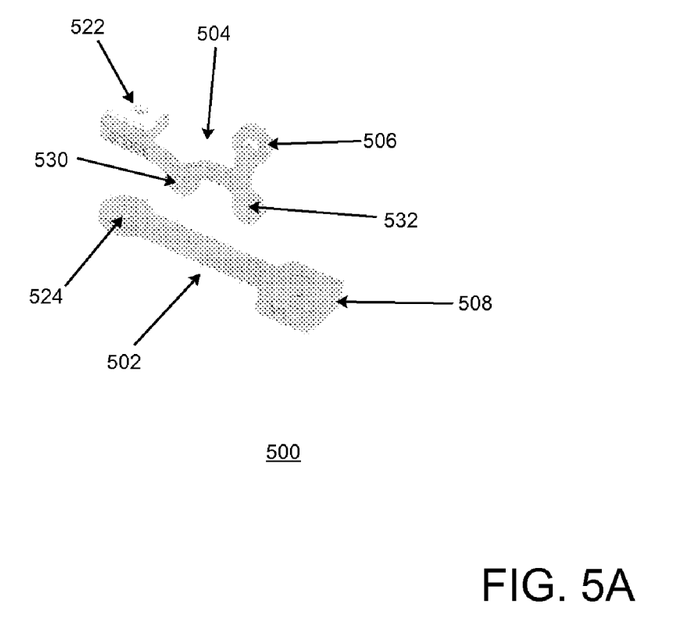
FIG. 5A illustrates an exploded perspective view of exemplary structural components of a tattoo machine according to yet a further embodiment of the invention, and including an exemplary two piece support sub-frame.

FIG. 5A illustrates an exploded perspective view of exemplary structural components of a tattoo machine according to yet a further embodiment of the invention, and including an exemplary two piece support sub-frame structure 500. The two piece sub-frame structure 500 comprises a base sub-frame 502 which has a lower end 524 and upper end 508. The lower end 524 may be adapted for attachment to an electrical wire contact as may be seen in FIGS. 1-3, such as for connection to a variable AC current power supply for powering the tattoo machine. The upper end 508 of the base sub-frame 502 may be configured, such as with a machined aperture or hole, for mounting a tube vise such as a screw-tight tube vise, for retaining a tube grip and guiding a needle bar through the upper end 508 between an armature bar and the tube grip, for example. In one embodiment, the base sub-frame 502 may be reversible, and the upper end 508 of the sub-frame may have an asymmetric thickness, such that when the base sub-frame 502 is reversed, the distance between an armature bar and a tube grip may be varied from one position to another, such as to allow for use of needle bars of varying length, for example.

The two piece sub-frame structure 500 also comprises an upper binding post/saddle sub-frame 504, which comprises a spring saddle mount 522 at a lower end thereof, and an upper binding post mount 506 at an upper end thereof. The upper binding post/saddle sub-frame 504 also comprises two coil mounting attachment points 530, 532 (such as holes for mounting screws or brackets) for structural attachment of the sub-frame 504 to one or more support coil assemblies, such as is shown in FIG. 1, for example.

Figure 5B:
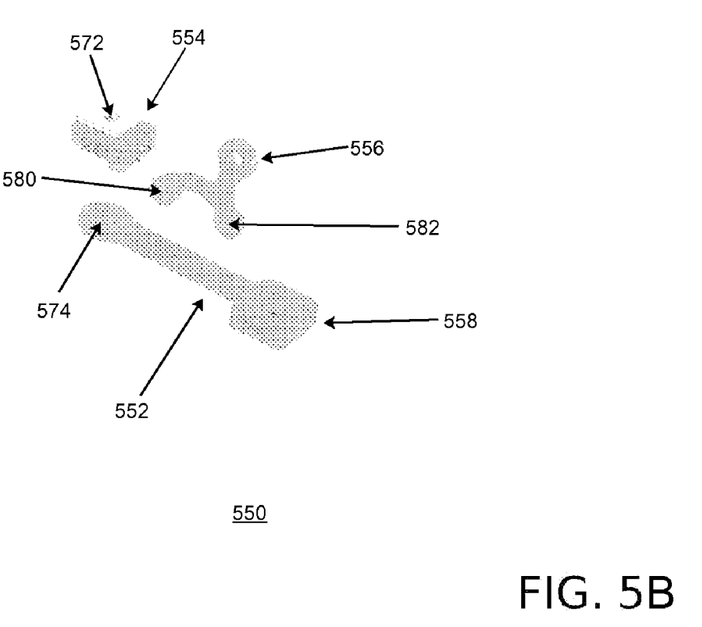
FIG. 5B illustrates an exploded perspective view of exemplary components of a tattoo machine according to another embodiment of the present invention, and including an exemplary three piece support sub-frame.

FIG. 5B illustrates an exploded perspective view of exemplary structural components of a tattoo machine according to yet a further embodiment of the invention, and including an exemplary three piece support sub-frame structure 550. The three piece sub-frame structure 550 comprises a base sub-frame 552 which has a lower end 574 and upper end 558. Similar to as described in reference to FIG. 5A above, the lower end 574 may be adapted for attachment to an electrical wire contact as may be seen in FIGS. 1-3, such as for connection to a variable AC current power supply for powering the tattoo machine. The upper end 558 of the base sub-frame 552 may be configured, such as with a machined aperture or hole, for mounting a tube vise such as a screw-tight tube vise, for retaining a tube grip and guiding a needle bar through the upper end 558 between an armature bar and the tube grip, for example. In one embodiment, the base sub-frame 552 may be reversible, and the upper end 558 of the sub-frame may have an asymmetric thickness, such that when the base sub-frame 552 is reversed, the distance between an armature bar and a tube grip may be varied from one position to another, such as to allow for use of needle bars of varying length, for example.

The three piece sub-frame structure 550 also comprises saddle, or spring saddle sub-frame 554, which comprises a spring saddle mount 572. The spring saddle mount 572 may be adapted for attachment to an armature bar and rear spring, so as to provide a spring-biased attachment of the armature bar, for allowing spring-biased reciprocating movement of the armature bar towards the electromagnetic support coil(s) via magnetic attraction. The spring saddle mount 572 may desirably also comprise at least one support coil mounting attachment point (such as one or more holes for mounting screws or brackets) for structural attachment of the saddle sub-frame 554 to a rear support coil assembly in a tattoo machine, such as is shown in FIGS. 2 and 3, for example.

The three piece sub-frame structure 550 also comprises an upper binding post sub-frame 556, which comprises an upper binding post mount at the upper end thereof. The upper binding post sub-frame 556 also comprises two coil mounting attachment points 580, 582 (such as holes for mounting screws or brackets) for structural attachment of the upper binding post sub-frame 556 to one or more support coil assemblies, such as is shown in FIGS. 2 and 3, for example.

Manufacturing and Assembly

According to one embodiment of the present invention, electromagnetic coil assemblies for use in a tattoo machine comprising aspects of the present invention may be manufactured according to an exemplary manufacturing process as follows. However, it is to be recognized that in other embodiments, other different manufacturing and assembly techniques, materials, equipment and procedures may be applied:

A coil core for a support coil assembly comprising an embodiment of the present invention may be manufactured such as by CNC machining or milling of a piece of 1010- to 1025-grade steel stock according to specifications to form a shape that appears substantially rectangular when viewed from the side and substantially square in cross section when viewed from the top. Grooves measuring about 1/16" by 1/16" may be machined completely around the steel coil core or post, about 1/4" down from the top and 1/8" up from the bottom, so that the grooves appear in the same place on all four sides of the post. For cores with square cross-sections, chamfered edges may be machined on the four angles between the machined grooves. In other embodiments, coil core members with non-square or rectangular cross-sectional shapes may be used, such as cores with substantially round, obround or other polygonal (such as hexagonal for example) cross-sectional shapes may be employed.

A hole may be drilled and tapped into the centre of one end of the post to a penetration depth of between 1/4" and 1/2" (recommended taps are 8-32 or 6-32), to provide for mounting of the coil assembly to a base sub-frame member. Holes may then be drilled horizontally through the 1/4" top flange of the coil core or post from side to side and then tapped (recommended tap is 6-32). If using a three piece sub-frame system, the rear coil assembly of the pair, in addition, may have 1 or 2 holes drilled, through the top 1/4" of the top flange of the coil core, from back to front—substantially perpendicularly to the holes drilled on the side, to a depth of about 3/8" and tapped with a recommended tap of 4-40. These holes are to receive mounting screws which will secure the spring saddle sub-frame component of a three piece sub-frame system (see FIGS. 3-5).

A layer of polyimide or other suitable insulation tape may be wrapped completely around the coil core or post so that it covers all four sides of the area between the machined grooves, including the chamfered edges, prior to winding of the coil windings. Plastic retaining washers measuring approximately 1" in diameter and 1/16" in thickness may be slid into the grooves at the top and bottom of the post. Three holes may then be drilled in each of the two retaining washers: one larger hole in the centre, measuring at least 1/4" in diameter; and two other smaller holes close to the outer edge of the washer and measuring at least 1/32" in diameter. Each retaining washer may be secured with a buna-n O-ring measuring about 1/16" in thickness, 3/8" in outside diameter, and 1/4" in inside diameter. The two O-rings may be inserted on top of the retaining washers under the edges of the machined grooves.

A steel coil core or post with polyimide tape, retaining washers, and O-rings (together referred to as a coil bobbin) may then be wound in magnetic copper wire in the area between the retaining washers, much like thread is wound around a bobbin in a sewing machine. The length of the magnetic wire winding may be varied depending on the size of the area to be wound, the thickness of the steel post, and the number of layers to be wound around the post. If used as the front support coil assembly, the coil may have between 4 and 11 layers of magnetic wire wound on the coil bobbin, and the back support coil assembly may have between 4 and 10 layers wound on the coil bobbin (the back coil may preferably have an even number of layers). The wire winding may be started from a small hole near an inner edge of the retaining washer and wound onto the polyimide insulation tape in layers from the bottom to the top and then back to the bottom, and so on until the desired number of layers is reached. The wire may exit through a small hole near an outer edge of the retaining washer at either end of the post, depending on whether an odd or even number of wire layers is used.

In an optional embodiment, any suitable form of or other thin protective layer tape may then be wrapped around the exterior of the magnetic copper wire winding to protect it. The ends of the wire may protrude from the smaller inner and outer holes in the retaining washers. A decal printed with a company logo or other image or graphic may also then be applied for aesthetic purposes.

Function

In one exemplary embodiment of the present invention, a tattoo machine incorporating at least one electromagnetic support coil and at least one attached sub-frame member may function substantially as follows:

When AC electrical current is delivered to one or more electromagnetic support coil assemblies, it passes through a magnetic copper wire that winds around the support coil cores or posts, magnetizing the steel coil core or post. Once magnetized, the coil core or post functions as an electromagnet, intermittently attracting an armature bar according to the frequency of the AC current. With the aid of resistance from one or more springs biasing the armature bar away from the electromagnetic support coil, the intermittent attraction and spring-biased release of the armature bar results in the vertical up-and-down reciprocating motion of the armature bar (similar to the motion of a sewing machine needle) and the attached needle bar. An auxiliary electrolytic axial capacitor may desirably work with the support coil assembly to store and release the electrical charges that pass through the assembly, smoothing and regulating AC current flow. The strength and duration of the AC current and therefore also the electromagnetic field generated by the support coil(s) may be controllably increased or decreased in strength using an adjustable AC electrical power supply, so as to allow for adjustment of the motion of the armature bar, and thereby the attached needle bar and needle grouping.

In a particular exemplary embodiment of the invention, the electromagnetic support coil assembly may be structurally attached to a two or three piece sub-frame support system, which may desirably comprise substantially non-ferrous sub-frame support members which are substantially non-ferromagnetic. The electromagnetic support coils may also be further separated and magnetically isolated with non-ferrous washers or spacers which are then attached to the said coils with non-ferrous fasteners, such as screws, to substantially isolate the magnetic components (electromagnetic support coils and armature bar—which are the most important parts of a functioning electromagnetic tattoo machine), thereby desirably reducing leakage and/or dissipation of the magnetic field generated by the coil assemblies, such as by absorption or influence of frame supports or screws—(which is a common problem in traditional tattoo machine technology incorporating a single separate one piece frame and fasteners which may be substantially ferromagnetic). Such isolation of the electromagnetic elements of the tattoo machine may desirably in turn increase and focus the magnetic field generated by the support coil assemblies on the armature bar which is mounted in a spring biased assembly (the only moving part on the machine which houses the needles and is directly responsible for the movement necessary for injecting the dye into the skin), thus improving the quality and controllability of the motion of the armature bar and performance of the tattoo machine.

According to further exemplary embodiments of the invention, further characteristics and advantages of the present inventive tattoo machine with electromagnetic support coils may include:

Weight reduction: The removal of a "middle section" of frame components extending between the upper and lower sides of the electromagnetic coils as are typically present in conventional tattoo machines, may advantageously reduce the weight of the tattoo machine apparatus as a whole. In addition, to further lighten the weight of the tattoo machine, any suitable lightweight material may be used to manufacture the support sub-frame members, such as but not limited to: plastics, composites, aluminum and titanium, for example.

Reversibility of upper binding post sub-frame: The threaded holes extending horizontally through the side of the top flange section of the electromagnetic support coils in certain embodiments of the invention may accommodate screws that secure the upper binding post sub-frame member to the support coil assemblies, may desirably allow the side upper binding post sub-frame member to be reversibly mounted on either side of the electromagnetic support coil assemblies to satisfy the demand for a "left handed" frame by "left handed" tattoo artists (when implementing a three piece sub-frame structure, for example). Such an ambidextrous option for assembling or reconfiguring a tattoo machine may not typically be possible on a standard "one piece" tattoo machine frame.

Reversibility of base sub-frame: The design of the base sub support member in certain embodiments of the present invention may be configured for use with a screw tight tube vice frame which has a "step" which houses a threaded rod/ferrule/nut system to secure tube grips. The reversible base sub-frame can be flipped to allow the tattoo machine to accept shorter or longer tubes based on the artist's preference. As a new standard is becoming adopted for commercially available "disposable" plastic tubes which only accommodate 4 ¾" needle bars, this feature is necessary to allow use of the new shorter needle bars. These embodiments may also be used with traditional metal tubes which house longer needle bars, which may be favored by some artists. In another embodiment, any suitable vice system may be implemented on the separate base sub-frame member of the present invention.

Performance adjustability: In certain embodiments utilizing a three piece sub-frame structure, the rear saddle sub-frame support member which may be made to support the rear spring, and may be secured to the rear electromagnetic support coil via tapped holes and screws, may be separated from the support coil assembly such as by being shimmed and therefore slid back away from the coil in order to slow down, or make softer, the impact of the reciprocating armature bar, if desired. This may provide additional adjustability of the operation of the tattoo machine according to an embodiment of the invention. In another embodiment, artists may have the option to mix and match separate sub-frame support members made from different materials in the same machine. Such as for example the use of an aluminum base sub-frame member with a plastic upper binding post sub-frame support member, and a steel saddle sub-frame member, for example. Alternatively, separately colored sub-frame support members may be mixed and matched according to aesthetic taste, for example.

In another embodiment, the separate sub-frame support members attached to the electromagnetic support coil of an inventive tattoo machine may also allow the operator to remove a spring saddle sub-frame member including the spring/armature bar assembly, without affecting the spring tuning of the tattoo machine or having to re-tune the tattoo machine after re-assembly. This is in contrast to on a conventional one-piece frame machine where standard removal of the spring itself, and then re-attaching the spring may result in changes to the placement of the spring resulting in the undesirable need to re-tune (adjust placement or tension (bend) of the spring) the machine before use.

The above description of several exemplary embodiments of the present invention is not intended to be exhaustive or to limit the embodiments of the invention to the precise forms disclosed herein. Although specific embodiments and examples are described herein for illustrative purposes and to allow others skilled in the art to comprehend their teachings, various equivalent modifications may be made without departing from the scope of the disclosure, as will be recognized by those skilled in the relevant art.

What is claimed is:

1. A tattoo machine comprising:
    at least one electromagnetic support coil assembly comprising a coil core having an upper end and a lower end, and at least one wire winding around said coil core, wherein said upper end of said coil core comprises a mounting flange;
    at least one upper sub-frame member structurally attached to and supported by said mounting flange of said coil core upper end;
    an armature bar attached to said at least one upper sub-frame member and adapted to move in a reciprocating manner towards and away from said upper end of said coil core; and
    a base sub-frame member structurally attached to and supported by said lower end of said coil core, wherein said base sub-frame member is adapted to support a needle tube.

2. The tattoo machine according to claim 1, wherein said coil core comprises at least one ferromagnetic material.

3. The tattoo machine according to claim 1, wherein said mounting flange of said coil core upper end comprises at least one threaded hole extending into a side surface of said mounting flange and wherein said mounting flange of said coil core upper end is structural attached to said at least one upper sub-frame member using one or more threaded fasteners.

4. The tattoo machine according to claim 3, wherein at least one of said threaded fasteners comprises a non-ferrous material.

5. The tattoo machine according to claim 1, wherein said coil core lower end comprises at least one threaded hole extending into said lower end of said coil core, and wherein said lower end of said coil core is structurally attached to said base sub-frame member using one or more threaded fasteners.

6. The tattoo machine according to claim 5, wherein at least one of said threaded fasteners comprises a non-ferrous material.

7. The tattoo machine according to claim 1, wherein said at least one upper sub-frame member comprises an upper binding post and a spring saddle mount, and wherein said armature bar is attached to said spring saddle mount.

8. The tattoo machine according to claim 1, wherein said at least one upper sub-frame member comprises an upper binding post sub-frame member comprising an upper binding post, and a saddle sub-frame member comprising a spring saddle mount, and wherein said armature bar is attached to said spring saddle mount of said saddle sub-frame member.

9. The tattoo machine according to claim 1, wherein said electromagnetic support coil core comprises a cross sectional shape selected from the list comprising: rectangular, square, round, obround, and quadrilateral.

10. The tattoo machine according to claim 1, wherein at least one of said base sub-frame member and said at least one upper sub-frame member comprise a non-ferrous material.

11. The tattoo machine according to claim 1, additionally comprising at least one non-ferrous spacer situated between said mounting flange of said coil core upper end and said at least one upper sub-frame member, and at least one non-ferrous spacer situated between said lower coil core end and said base sub-frame member.

12. The tattoo machine according to claim 1, wherein said base sub-frame member additionally comprises a tube vice adapted to support a needle tube.

13. The tattoo machine according to claim 12, wherein said tube vice comprises a screw-tight tube vice comprising an internal ferrule.

14. An electromagnetic support coil assembly for a tattoo machine comprising:
- a coil core having an upper end and a lower end;
- at least one wire winding around said coil core;
- wherein said upper end of said coil core comprises a mounting flange having at least one threaded hole extending into a side surface of said mounting flange adapted for supportive structural attachment to at least one tattoo machine upper sub-frame member using one or more threaded fasteners; and wherein said lower end of said coil core comprises at least one threaded hole extending into said lower end of said coil core and is adapted for supportive structural attachment to a tattoo machine base sub-frame member using one or more threaded fasteners.

15. The electromagnetic support coil assembly according to claim 14, wherein said coil core comprises at least one ferromagnetic material.

16. The electromagnetic support coil assembly according to claim 14, wherein said coil core comprises a cross sectional shape selected from the list comprising: rectangular, square, round, obround, and quadrilateral.

17. The electromagnetic support coil assembly according to claim 14, wherein said coil core additionally comprises a first circumferential transverse groove proximal to said mounting flange of said upper end of said coil core, and a second circumferential transverse groove proximal to said lower end of said coil core.

18. The electromagnetic support coil assembly according to claim 17, additionally comprising first and second removable washer seated in said first and second grooves, wherein said at least one wire winding is retained between said first and second removable washers.

19. The electromagnetic support coil assembly according to claim 14, wherein said coil core additionally comprises at least one layer of insulating tape around at least a portion of said coil core, wherein said insulating tape is situated between said coil core and said at least one wire winding.

20. The electromagnetic support coil assembly according to claim 14, wherein said at least one wire winding comprises copper magnetic wire.

* * * * *